United States Patent
Walzman

(10) Patent No.: US 10,610,672 B2
(45) Date of Patent: Apr. 7, 2020

(54) BULGING TORUS BALLOON

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 165 days.

(21) Appl. No.: 15/932,766

(22) Filed: Apr. 23, 2018

(65) Prior Publication Data

US 2019/0321602 A1    Oct. 24, 2019

(51) Int. Cl.
*A61M 25/10*     (2013.01)
*A61M 25/00*     (2006.01)

(52) U.S. Cl.
CPC ....... *A61M 25/1002* (2013.01); *A61M 25/104* (2013.01); *A61M 2025/1061* (2013.01); *A61M 2025/1095* (2013.01); *A61M 2025/1097* (2013.01)

(58) Field of Classification Search
CPC ............ A61M 25/1002; A61M 25/104; A61M 2025/1061; A61M 2025/1095
See application file for complete search history.

(56) References Cited

U.S. PATENT DOCUMENTS

| | | | |
|---|---|---|---|
| 5,147,302 A | 9/1992 | Euteneuer et al. | |
| 5,639,274 A | 6/1997 | Fischell et al. | |
| 6,129,704 A | 10/2000 | Forman et al. | |
| 6,296,655 B1 | 10/2001 | Gaudoin et al. | |
| 8,480,619 B2 | 7/2013 | Porter | |
| 9,993,325 B2 * | 6/2018 | Ren | A61F 2/013 |

* cited by examiner

*Primary Examiner* — Julian W Woo

(57) ABSTRACT

A method for use of a medical device that anchors itself and other medical devices while channeling blood flow through the center of a vessel proximal to the device's target area to minimize debris and pressure necessary to move blood proximal to the device, resulting in superior recoil reduction capabilities. The profile is a bulging torus or doughnut-shaped balloon inflatable and deflatable by increasing and decreasing pressure within the toroidal balloon, having two passages therethrough, one passage dimensioned to accommodate blood flow, the other dimensioned for a delivery device.

4 Claims, 4 Drawing Sheets

BULGING TORUS BALLOON

FIELD OF THE INVENTION

The present invention relates generally to medical device used in medical procedure, specifically to a cylindrical balloon to ameliorate ischemic injury during balloon inflations.

BACKGROUND OF THE INVENTION

Discussion of the Prior Art

The use of devices in conjunction with medical procedures for controlling blood flow in a blood vessel is taught by the prior art. Among the most common is a balloon catheter. The balloon catheter, such as taught in the prior art, may be used to achieve isolation of a body part from its blood supply. Balloons can also be used sometimes to help pin another device in a certain position temporarily.

One of the problems associated with using balloons is that although control of the blood flow through a portion of the blood vessel is achieved, including blockage of the blood supply to a targeted site, blood flow is completely interrupted to other sites near the targeted site. This shortcoming can be tolerated for a short duration because when one blood vessel becomes blocked, the body normally increases the blood flow through other, essentially paralleling blood vessels. However, complex medical procedures may not be achieved during said short duration resulting in injury to said other sites or requiring multiple operations at the same targeted site.

Other problems associated with balloons include the number of positioning changes required each time a balloon is deflated to allow flow, to avoid ischemia. The prior art also results in longer procedure time, increased radiation exposure for the patients and staff, as well as increased risk of morbidity. Furthermore, in some vessels blood flow is so critical that temporary balloon occlusion for even relatively short periods of time is not tolerated. This limits the ability to use balloons to pin catheters or other devices for support in such vessels, resulting often in unwanted recoil of said device, and the inability to efficiently, effectively and safely achieve the procedural goal. The present invention surmounts the problem of complete blood interruption to other sites near the targeted site.

Fluid dynamics associated blood vessels and catheters interaction causes recoil and displacement. The catheter is pushed back or recoils and displaced as a result of the velocity of the fluid and vessel walls it encounters. It is particularly acute when using a catheter of small size, e.g. less than about 4 French, which are prone to severe whipping and recoil. The present invention ameliorates the problem of displacement and recoil. Additionally, in many anatomical situation access to some vessels can be difficult. This is especially the case when tortuosity and/or the particular anatomy creates additional bends along the desired course of the catheter. In such cases, when a wire is advanced around the bend, a counterforce is created that tends to kick back the wire and catheter that the wire is being advanced through. If the catheter does not have adequate physical support to resist such kickback, it will fall out of the desired position. In some cases this could prevent appropriate access to the desired pathological region altogether. In other cases, it can create complications during a procedure when catheters and devices suddenly kickback and are dislodged from the desired location. Such movement is undesirable.

Prior art teaches the use of balloons to stabilize catheters and guide catheter within the vessel for device control. Typically, said balloons block the entire vessel when deployed.

SUMMARY OF THE INVENTION

The present invention provides an improved anchoring device and method for catheters and other medical devices. It may be deployed for use in blood vessels and other hollow tubular organs within a patient's body. Said anchoring device comprises a bulging torus-shaped balloon with two passages.

The present invention specifically improves upon existing medical-balloon technology by including two passages through the present invention, as compared to a single passage as taught by the prior art. In addition, while some prior art teaches multiple balloons around a central catheter, which have the possibility of channeling blood around the catheter next to the walls of the vessel in which the balloon-surrounded catheter is located, the present invention channels the blood through the center of the vessel in which the present invention is located.

The present invention offers several dramatic improvements over the prior art. These include first, by channeling the blood down the center of the vessel, the blood is prevented from shearing off debris from the vessel walls, thus preventing the difficulties associated with adding debris to a bloodstream. Second, by channeling the blood down the center of the vessel, less pressure is necessary to move the blood to where it is intended, thus reducing the difficulties associated with elevated blood pressure. Third, the shape of the device of the present invention minimizes recoil and displacement. Fourth, the current device allows continued blood flow through said balloon, and thus through the vessel it is deployed in, even when said balloon is fully inflated.

The present invention can also combine a temporary bulging torus shaped balloon and another unique support catheter or procedural catheter. For example, the balloon of the current invention can be deployed across the origin of an injured and bleeding branch artery, to ameliorate said bleeding, while allowing continued blood flow in the parent artery, through the central hole/lumen of said bulging torus/cylinder balloon. In another embodiment, a bulging torus balloon can be used in the aorta to pin a second catheter in position within the origin of one of the great vessels, to prevent recoil of said second catheter into the aorta while wires or other devices are advanced distally through said second catheter. In some procedures this can allow adequate distal wire access to subsequently allow further egress of said second catheter towards a target location, over said wire.

In order to prevent recoil and displacement, the present invention deploys a bulging torus shaped balloon which is inflated until said balloon fit snuggly against the inside of the vessel in which the present invention is deployed, thus allowing the support for fixing the catheter element of the present invention, or a second catheter or other device that is delivered separately alongside it. Said balloon is affixed to the catheter element of the present invention. The medical device disclosed by the present invention teaches a unique vessel-anchoring shape which combines static and dynamic features to ameliorate recoil and displacement. In particular, the cylindrical outer surface allows for maximum friction while blood flowing through the center of the device provides additional radial force to enhance anchoring. The present invention teaches both the use of a passage shaped by a cylindrical element as well as a passage shaped by a truncated cone.

More particularly, the current invention teaches an embodiment wherein said first passage has a blood-entry hole which is greater in size than the blood-exit hole at the other end of said passage. Such an alignment forms a truncated conical section which enhances the radial anchoring force resulting from blood flowing into a larger opening than it exits.

Said balloon element is located at any point along a delivery hypotube/catheter or other device capable of delivering the balloon of the current invention. The delivery device or catheter must include least one port that is capable of overlapping a corresponding port within the second passage of the present invention. Said ports facilitates the delivery and remove of fluid or air into and out of said balloon, in order to inflate and deflate said balloon as desired.

The port in the second passage may be simply one or more holes or may be a more complex governing element. Such a governing element may be valve-activated due to pressure or external stimuli, such as radio waves. Said port may have the capability of allowing said liquid or activatable foam to be introduced into the present invention outside the patient's body to form a seal and act as an activation and deactivation device.

Additionally, in some embodiments, said balloon can be used to perform angioplasty and open a blockage. There is a critical advantage to this device in that it allows temporary flow of blood to avoid ischemic injury, with immediate restoration of a degree of flow beyond a vessel blockage. This will allow additional time to remove or dissolve a clot while allowing flow to the at-risk tissue. Additionally, in the case of pulmonary emboli which are large there is an additional issue of heart strain due to the lack of outflow from the right side of the heart, the balloon described here can be deployed within the pulmonary embolus and can also help relieve such heart strain by allowing outflow from the right heart past said clot when there are large pulmonary emboli in the main pulmonary arteries. Additionally, the balloon of the current invention can be used for balloon-assisted embolization.

DETAILED DESCRIPTION OF THE INVENTION

The present invention is composed of a temporarily bulging torus shaped bypass balloon 10 comprising two passages. One passage further comprises a port.

The outer diameter of said balloon is 0.001 cm-30 cm. The inner diameter of said balloon element is 0.0001 cm-29 cm.

Figure 1:
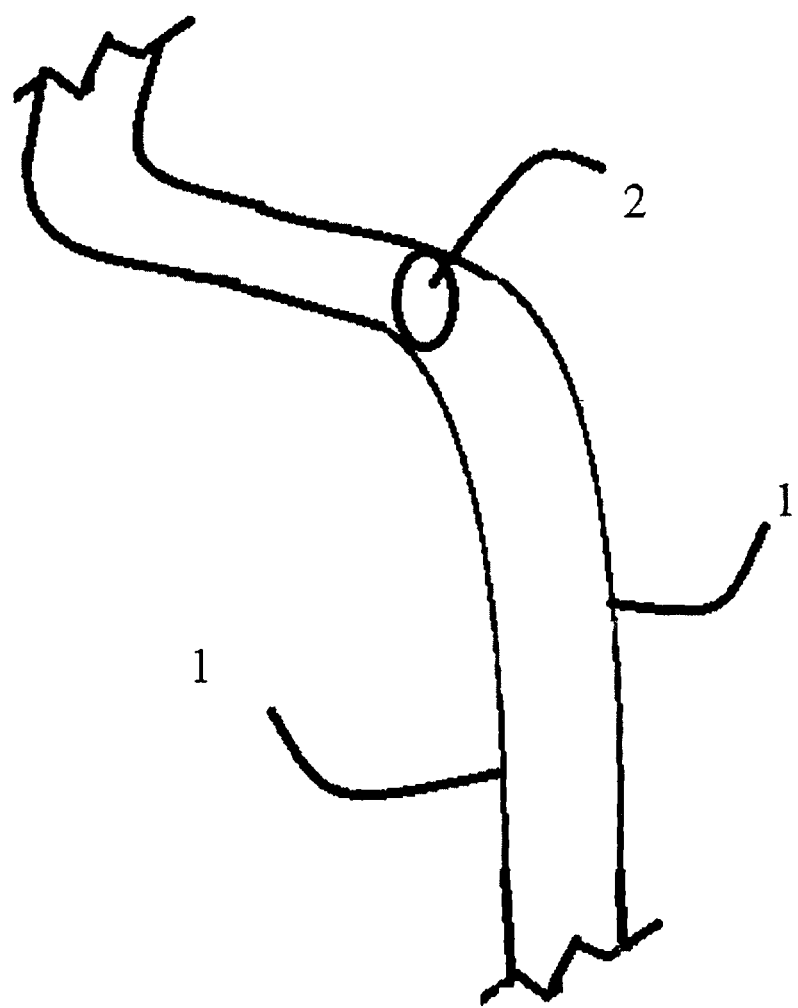
FIG. 1 vessel 1 with blockage 2.
Figure 2:
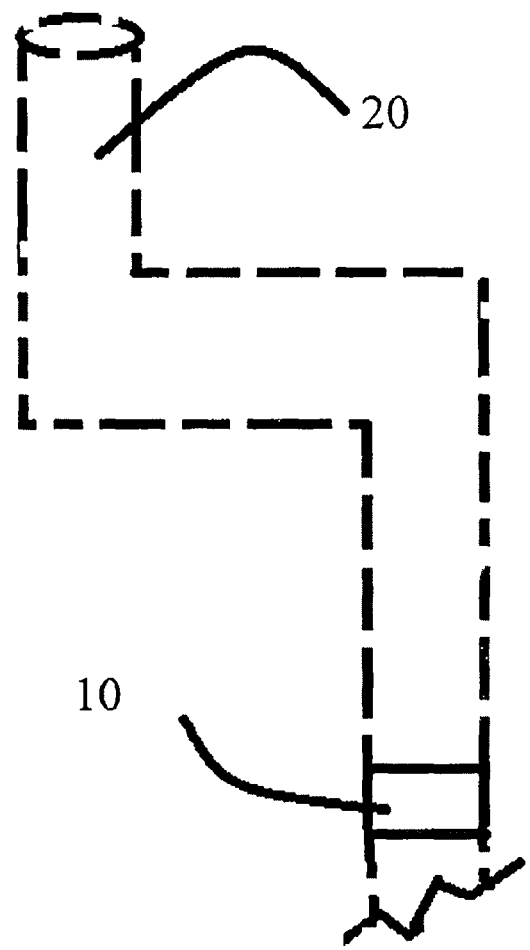
FIG. 2 un-deployed bulging torus balloon
FIG. 3 deployed bulging torus balloon
FIG. 4 deployed bulging torus balloon in vessel with blockage 2.

The present invention is capable of inflating and deflating prior to deployment within a vessel wall 1. Referring to FIG. 2, the bulging torus-shaped balloon 10 of the current invention is depicted in a deflated state disposed upon delivery catheter 20 (shown with dotted lines as not part of the invention).

Figure 3:
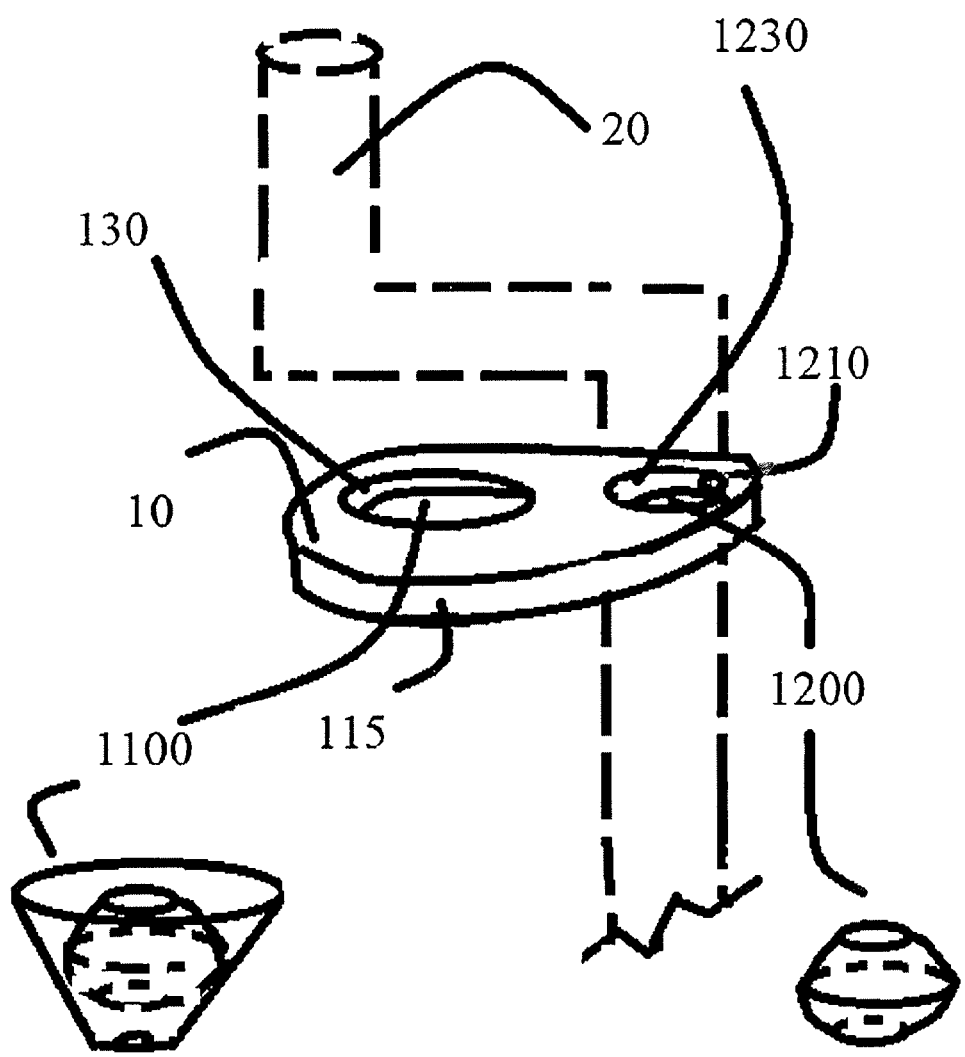

FIG. 3 depicts the bulging torus-shaped balloon 10 in a fully inflated, deployed state disposed upon delivery catheter 20 (shown with dotted lines). Second passage 1200 allows the delivery device 20 to pass therethrough. First passage 1100 allows for blood to flow through the center of the present invention. Port 1210 within second passage 1200, more particularly on second passage interior wall 1230, overlaps in use with a corresponding port (not shown) on delivery device 20. Balloon surface 115 presses against a vessel wall (not shown) to anchor the present invention and any associated devices such as catheters at a desired location. First passage surface 130 may be shaped to use blood flow to create radial pressure toward the blood vessel wall, thus enhancing the anchoring capability of the present device 10.

Figure 4:
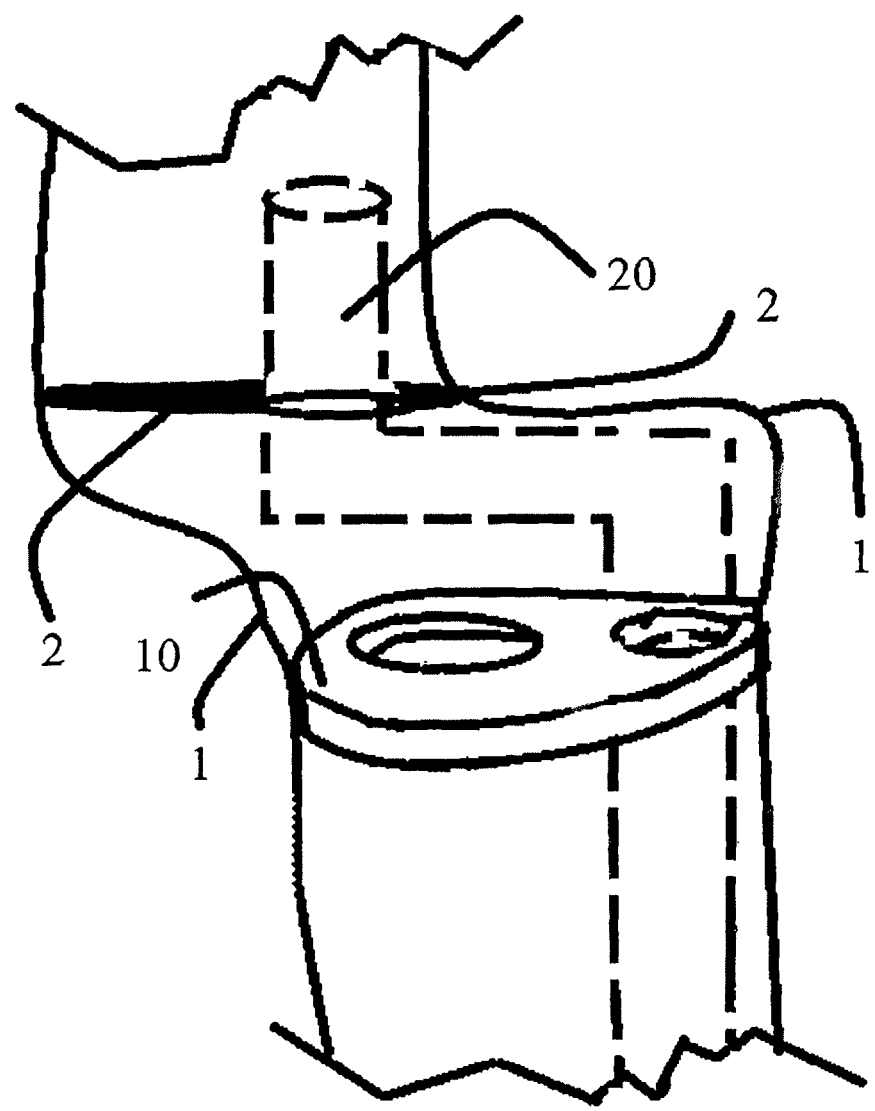

Referring now to FIG. 4, the balloon of the present invention 10 is deployed with delivery catheter 20 inside blood vessel wall 1. Blockage 2 is also depicted.

The bulging torus-shaped balloon 10 of the present invention is capable of supporting a catheter 20 or other devices at a particular location/position within a vessel wall 1 or other organ (not shown).

The present invention's balloon element can be added to other catheters or support catheters such as described by Dr. Daniel Walzman's prior applications, in order to help support said catheters in a particular position, and to prevent recoil and displacement.

The present invention may use a catheter as a delivery device. It may also be delivered by a non-catheter device such as a wire which is capable of moving the present invention to the targeted position, activating the preloaded, expandable and contractible material in the balloon, and being replaced by a catheter. Such expandable and contractible material may be activatable foam.

The disclosed bulging torus-shaped balloon 10 may be used by the following method, comprising the steps of:
(a) folding the bulging toroidal balloon 10:
(b) inserting a delivery device through said second passage of the bulging toroidal balloon so as to form a ninety-degree orientation with respect to a surface wall of the balloon, and to overlap the perimeter of said port in the second passage of the balloon with the perimeter of a port on said delivery device;
(c) inflating the budging torus shaped balloon by ejecting liquid into the balloon from the delivery device;
(d) deflating the budging torus shaped balloon by vacuuming or suctioning the liquid from the balloon into the delivery device;
(e) inserting the delivery device and the bulging torus-shaped balloon into a blood vessel;
(f) maneuvering the delivery device so as to position the torus-shaped balloon to targeted location;
(g) inflating the budging torus-shaped balloon by ejecting the liquid from the delivery device;
(h) deflating the budging torus shaped balloon by vacuuming or suctioning the liquid of the torus-shaped balloon into the delivery device; and
(i) removing the delivery device and the balloon via the blood vessel of the targeted location.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of using, a bulging toroidal balloon, wherein said bulging toroidal balloon may be inflated by increasing pressure within said balloon, deflated by decreasing pressure within said balloon, said balloon comprising:
   i) a first passage;
   ii) a second passage;
   iii) a liquid capable of flowing into and out of said balloon between external and internal walls of said balloon for inflation of said balloon;
   iv) a port in said second passage;
   v) wherein said port is configured to communicate with a catheter port in a delivery device;
   vi) wherein said bulging toroidal balloon has an external surface wall, an internal surface wall, and connecting surface walls linking between both external and internal surface walls,
      wherein said first passage is of sufficient size to allow blood to flow through when said bulging toroidal balloon is sufficiently inflated; and
      wherein said second passage is of sufficient size to allow said delivery device to pass through; and
      wherein said bulging toroidal balloon provides a form for said liquid to flow from said catheter port through said second passage port to inflate said balloon, and then to deflate said balloon by liquid flowing from said second passage port into said catheter port;
   said method comprising the steps of:
      (a) folding said bulging toroidal balloon;
      (b) inserting said delivery device through said second passage of said balloon so as to form a ninety-degree orientation with respect to a connecting surface wall of said balloon and to overlap the perimeter of said port in said second passage of said balloon with the perimeter of a port on said delivery device;
      (c) inflating said bulging toroidal balloon by ejecting said liquid from said delivery device;
      (d) deflating said bulging toroidal balloon by vacuuming or suctioning said liquid of said balloon into said delivery device;
      (e) inserting said delivery device and said balloon into a blood vessel;
      (f) maneuvering said delivery device so as to position said balloon to targeted location;
      (g) inflating said bulging toroidal balloon by ejecting said liquid of thereinto from said delivery device;
      (h) deflating said bulging toroidal balloon by vacuuming said liquid of said balloon into said delivery device; and
      (i) removing said delivery device and said balloon via said blood vessel.

2. The bulging toroidal balloon of the method of claim 1, wherein said first passage and said second passage are configured so as to allow blood or said delivery device to pass perpendicularly through said bulging toroidal balloon.

3. The bulging toroidal balloon of the method of claim 1, wherein said first passage is shaped as the exterior of a truncated cone such that blood flow into a decreasing circumferential passage enhances radial anchoring force.

4. The bulging toroidal balloon of the method of claim 1, wherein said port in said second passage is a governing element.

* * * * *